United States Patent [19]
Carver

[11] Patent Number: 4,853,614
[45] Date of Patent: Aug. 1, 1989

[54] METHOD AND APPARATUS FOR MEASURING MOISTURE CONTENT OF GRANULAR MATERIAL

[76] Inventor: Robert L. Carver, 1884 Glengary Rd., Akron, Ohio 44313

[21] Appl. No.: 166,623

[22] Filed: Mar. 11, 1988

[51] Int. Cl.$^4$ .................................. G01R 27/26
[52] U.S. Cl. ........................... 324/61 R; 324/61 P; 324/61 QS
[58] Field of Search ............. 324/61 R, 61 P, 96, 324/127, 65 R, 61 QS, 61 QL; 340/870.37; 73/336.5

[56] References Cited

U.S. PATENT DOCUMENTS

| | | | |
|---|---|---|---|
| 2,665,409 | 1/1954 | Rogers | 324/61 R |
| 3,046,479 | 7/1962 | Mead et al. | 324/61 QS |
| 3,389,601 | 6/1968 | Semplak | 324/61 P |
| 3,811,087 | 5/1974 | Schmelzer | 324/61 P |
| 4,228,393 | 10/1980 | Pile | 324/61 QS |
| 4,259,632 | 3/1981 | Ahtiainen | 324/61 QL |
| 4,403,191 | 9/1983 | Satake | 324/61 R |
| 4,502,937 | 3/1985 | Yagi | 324/96 |
| 4,503,424 | 3/1985 | Evenwoll | 324/61 P |
| 4,675,596 | 6/1987 | Smith | 324/61 QS |

OTHER PUBLICATIONS

Mark's Standard Handbook for Mech. Engrs., 8th Ed., McGraw Hill Book, Co., 1979, pp. 6–161 (Table 1).

Primary Examiner—Reinhard J. Eisenzopf
Assistant Examiner—Anthony L. Miele
Attorney, Agent, or Firm—Oldham & Oldham Co.

[57] ABSTRACT

A method and apparatus for measuring the moisture content of a material wherein the measuring apparatus is positioned within a falling stream of the material to thereby continuously sample the material. The mounting angle and sideboard geometry of the apparatus are selected to give equivalent of in-bin mounting in terms of density and void to solid ratio variation so that accurate measurements may be obtained. The position of the apparatus is such that sample integrity may be visually verified and measurement error by improper sampling avoided. The method and apparatus are particularly advantageous in the manufacture of concrete wherein moisture content of sand or other granular material incorporated into the concrete must be accurately determined. The present invention allows the moisture measurement to be carried out as an in-line proceedure in the manufacturing process.

23 Claims, 6 Drawing Sheets

CAPACITANCE VARIATION
VERSUS H2O.

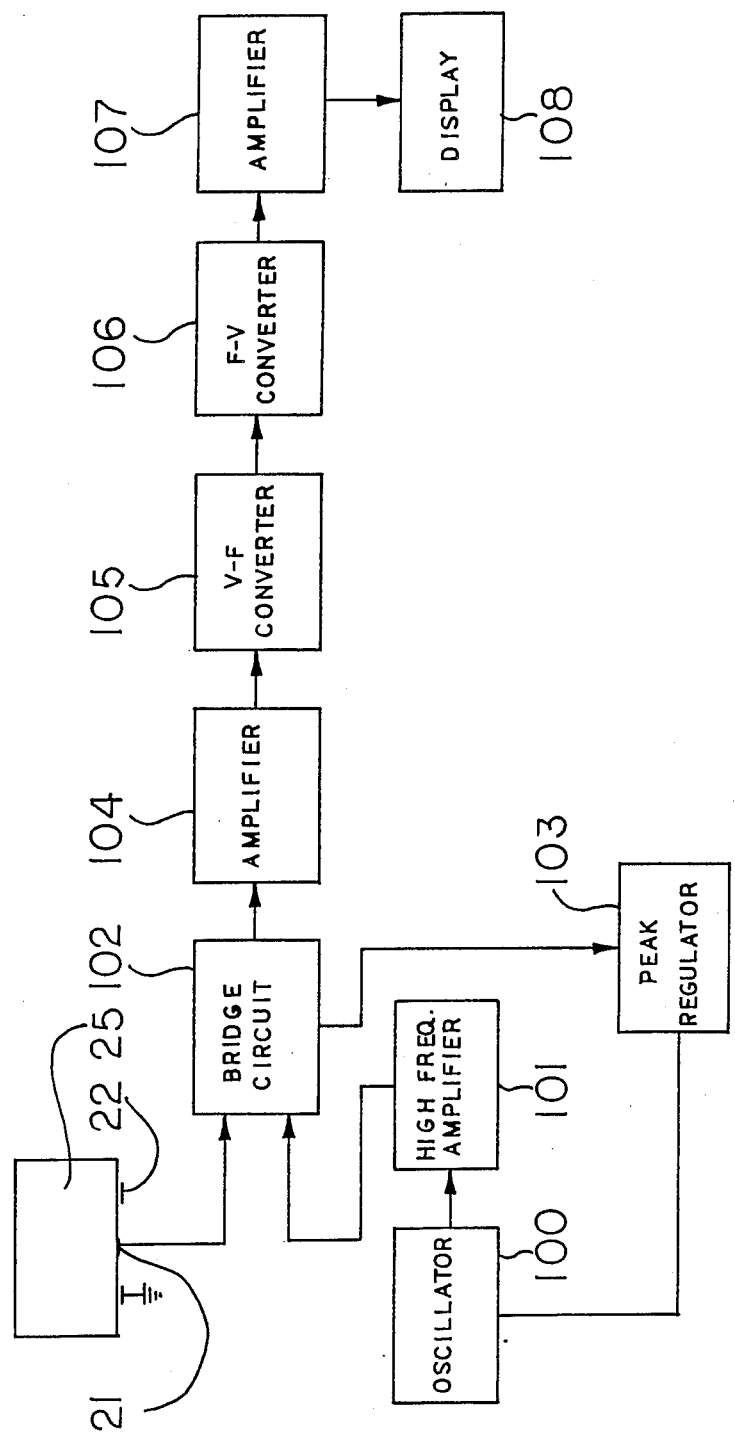

FIG.7B
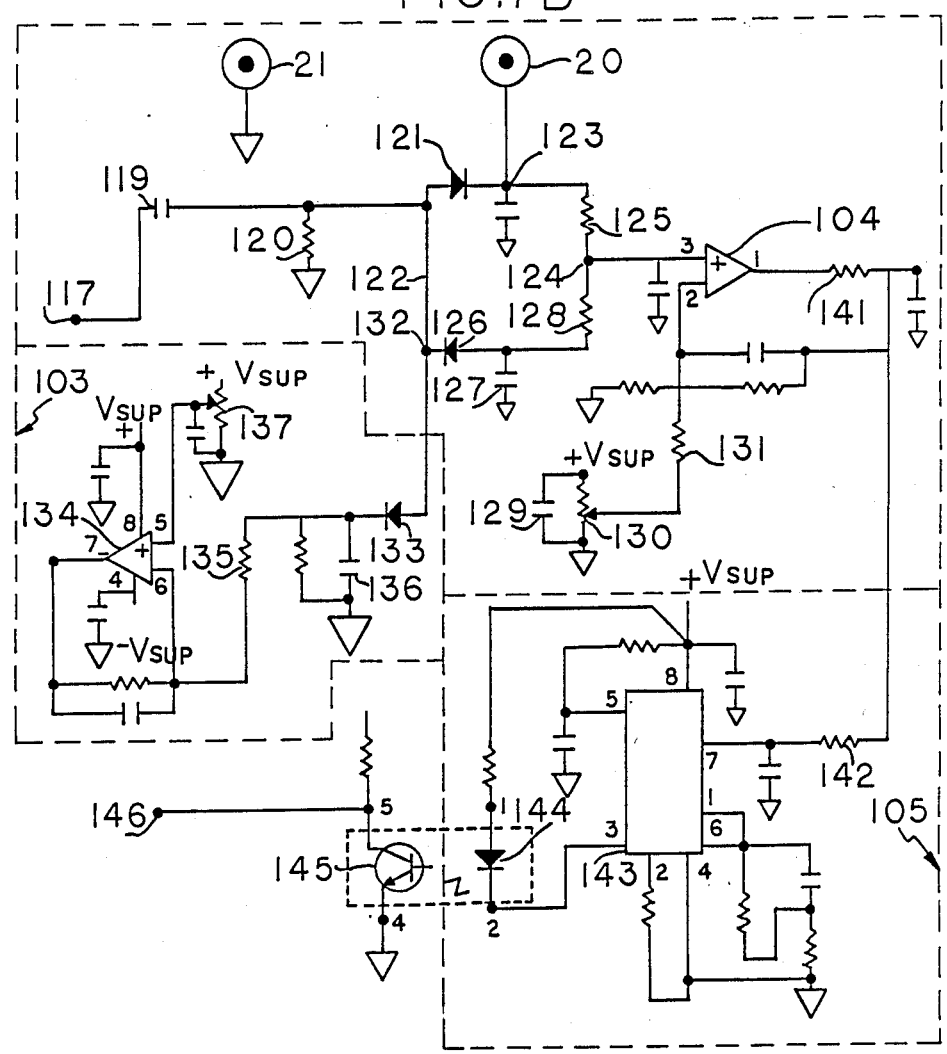
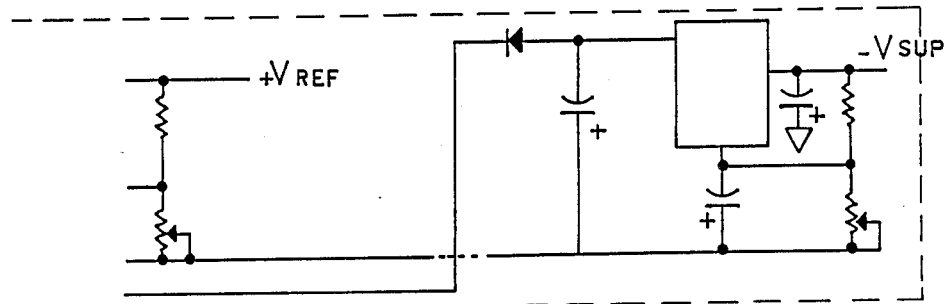

METHOD AND APPARATUS FOR MEASURING MOISTURE CONTENT OF GRANULAR MATERIAL

BACKGROUND OF THE INVENTION

This invention relates generally to methods and apparatus for the measurement of the moisture content of a granular material, such as sand or other mineral aggregates which may be used for making concrete or in other applications. More particularly, the invention relates to measurement of the moisture content in a granular material wherein such measurement yields an accurate determination of the moisture in a particular batch of the granular material. A sample of the granular material is measured using a fringe electrode capacitance type gauge which is mounted at a physical location where sampling integrity can be visually verified, thus giving increased accuracy with a much simplified system.

In the concrete products manufacturing area, such as ready-mix batch plants and block plants, it is well known that the water content of a cement concrete mixture has a significant effect on the strength and durability of the cement product after hardening. In many applications the water content of the cement mixture must be very accurately known in order to obtain the proper physical characteristics of the resultant concrete mixture.

It has been found that the problem of measuring with sufficient accuracy the amount of water incorporated into a concrete mixture has been less than satisfactory, especially in manufacturing areas where large amounts of the materials used in the concrete mixture are handled. A ready-mix concrete batch plant, for example, may typically have one hundred concrete recipes for different applications and uses. In most of the recipes, sand, one or more rock aggregates, cement, water, fly ash, and other additives are utilized in large amounts. The ratio between the aggregates and other ingredients is varied in a specific predetermined manner to suit the application and weather conditions in which it is to be used. It is standard practice that such concrete recipes are formulated on the basis of a percentage of ingredients based on their dry weight. Problems arise due to the fact that the rock and sand aggregates are stored in open stock piles, thereby being exposed to moisture, and retaining some moisture in surface moisture. The water introduced as surface moisture as sand, gravel and coarse and fine aggregates may be as much as fifty percent of the total requirements of water necessary in the particular recipe. It is thus essential, in order to batch concrete accurately, that the amount of surface moisture in the aggregates or granular materials be determined for each batch.

It is generally agreed that the rock aggregate surface moisture is relatively constant and therefore an accurate estimate of its surface moisture can safely be used. On the other hand, the surface moisture found in the sand to be mixed with the batch can easily vary from two to ten percent within the stock pile dependent upon the conditions of rain, sunshine or other environmental conditions. The surface moisture of the sand must therefore be accurately determined to eliminate any source of error introduced thereby.

In manufacturing plants which produce batches of concrete it is sometimes necessary to handle up to a ton of sand per minute in order to meet the requirements of the concrete mixers. Alternately, if a batcher is feeding ingredients of the concrete into truck mixers, which mix the batches during transit to the job site, the feed must keep pace with which the trucks can be loaded which is also a very rapid operation. As mentioned hereinbefore, the specifications of a particular concrete batch must be determined very accurately, especially the determination of the amount of water found as surface water on the ingredients. With both stationary central plant mixers and transit mixers, it is usual to utilize a conventional moisture gauge which is mounted inside the bin serving a weigh hopper in which the ingredients are distributed. A moisture gauge is positioned in such a way as to sample the flow of the ingredients in the bin. It has been found with such mounting that the attempt to sample the flow is only an estimation, and sample integrity is not maintained and cannot be monitored. There has been no easy way to verify the flow sampling position of the sensing surface inside the bin thereby creating errors which cannot be tolerated. It is estimated that at least fifty percent of the installed moisture gauges in concrete batch plants are installed in non-flowing sections of the bin.

The operator of the plant who is trying to produce good concrete with predictable slump at the job site requires moisture measurement of the granular materials, and especially of the sand in the batch, to a high degree of accuracy. Many previous attempts found in the prior art yield a moisture measurement of the sand in a static section of the bin which is of no value to the operator.

Previously in the prior art, measurements of the moisture content of sand or other granular materials have utilized measurements of the electrical resistivity and the dielectric properties of the material. It has been found with electrical resistivity measurements, that accurate moisture content can only be determined if the packing of the sand is uniform and the moisture is uniformly distributed through the sand. Such conditions generally do not exist, and therefore more accurate measurements are desired. Alternatively, the dielectric measurements are quite sensitive to the total moisture content of the material, and provide a more accurate determination than resistivity measurements.

It is therefore found to be desirable to provide placement of a measuring apparatus such that sampling of the sand used in a batch of concrete, for example, may be visibly monitored and verified. Additionally, it is desired that a measuring apparatus be designed such that its use does not inhibit or add steps to the manufacturing process.

SUMMARY OF THE INVENTION

It is the broad object of the present invention to provide a very accurate measurement of the moisture content of sand or similar granular material by the elimination of sources of error found in previous measuring methods. More particularly, it is desired to obtain a very accurate measurement of the moisture content of sand or similar materials utilized in the manufacture of concrete batches.

It is another object of the present invention to provide placement of a measuring apparatus such that sampling in the flow of the granular materials during weighing and mixing can be visibly verified to insure sample integrity. In this way the measuring apparatus is always sampling the sand used in a current batch of materials, and measurement of the sand in a static condition is avoided.

It is a further object of the present invention to provide a measuring apparatus designed in accordance with the desired sampling of the material in which sample integrity may be verified, and utilized with the desired measuring method.

In accordance with the present invention, a method and apparatus for the continuous measurement of the moisture content of a sand or other granular material in a particular batch of the material is provided. The invention utilizes a capacitance measuring device, and more particularly a fringe electrode capacitance type geometry for the sensing elements, which will determine the dielectric properties and moisture content of the measured material. The sensing arrangement is housed within a sampling apparatus comprising a trough, which is mounted in an angular position such that the material to be measured may simply be made to fall into the sampling apparatus as it travels to a weighing or mixing bin. The sampling apparatus is constructed in a particular manner to insure accurate and uniform sampling of the material as it falls through the apparatus, and enables visible determination of the sample integrity along with providing easy access to the sensing arrangement for calibration and/or repair.

With the manufacture of concrete, the accurate knowledge of the total moisture of the entire batch of material to be used will thus ensure the manufacture of concrete mixes which have accurately known compositions. It is to be understood, though, that the moisture measurement of sand and other granular materials in the manufacture of concrete is only one area in which the present invention may be useful. Alternatively, for example, cinder plants or an agglomerate manufacturer would be facilitated by use of the present invention to determine moisture content of these particular granular materials.

The foregoing and other objects are achieved by the present invention utilizing a significantly simpler method and apparatus which is easily incorporated into a manufacturing process without limiting the process thereby. The present invention is also found to achieve greater accuracy and reliability than previous attempts found in the prior art.

BRIEF DESCRIPTION OF THE DRAWING

For an understanding of the scope of the invention and a complete understanding of the objects, techniques and structure of the invention, reference should be made to the following detailed description and the accompanying drawings wherein:

FIG. 6 is a block diagram illustrating a preferred electrical system for the measuring circuit of the present invention;

FIG. 7a and 7b are schematic circuit diagrams of a moisture measuring circuit in accordance with this invention;

It is to be understood that like reference characters designate like or corresponding parts throughout the several views as shown in the figures.

DETAILED DESCRIPTION OF THE PREFERRED EMBODIMENTS

Referring now in detail to the drawings, and in particular to FIGS. 1-4, a measuring apparatus designated generally as 10 is utilized for use in measuring the moisture content of granular materials.

Figure 1:
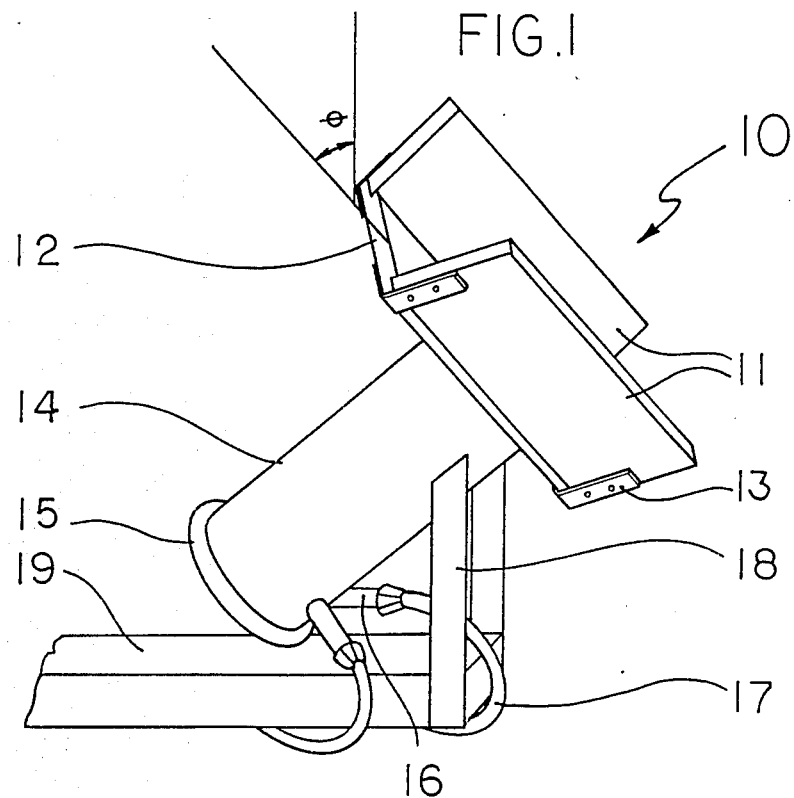
FIG. 1 is a perspective view of the apparatus of the present invention utilized for measuring moisture content.

With reference to FIG. 1, the preferred embodiment of the moisture measuring apparatus 10, in accordance with the present invention is illustrated, in which a trough is formed having two sideboards 11 and bottom 12 which forms a sensing surface. The sideboards 11 and bottom 12 are held together by means of brackets 13. A housing 14 encases the electronic measuring circuitry, and is closed by cover 15. The housing 14 is provided with input/output terminals 16 whereby measurements or power may be coupled out of or into the measuring circuit via lines 17.

In the preferred embodiment, sideboards 11 and sensing surface 12 are formed of a ultra high molecular weight polyethylene material (UHMW) which is used for all exposed plastic surfaces in the sensing area. It has been found that the material selected for mechanically supporting the sensing elements of the present invention and which make up the trough, are critical to obtain accurate measurements. The requirements of such material are that it be an excellent electrical insulator at the operating conditions of the measuring apparatus, as well as mechanically rigid enough to allow gasketing and proper securing to a support structure. The material also must have outstanding abrasion resistance to withstand exposure to a wide variety of materials as they fall into and through the trough. In this way the material acts as a wear plate to protect the sensing equipment, and extend the useful life of the measuring instrument. The material also must have a low water absorption, as well as a low and predictable dielectric constant so that the instrument may be easily and accurately calibrated. Along with these characteristics, it is a prerequisite that the material have a low coefficient of friction to prevent the buildup of any materials on the sensing surface to avoid error and retain sample integrity. All these characteristics are met by the use of ultra high molecular weight polyethylene, but it is to be understood that the present invention is not limited thereby and other materials may be used if these requirements are met.

Figure 2:
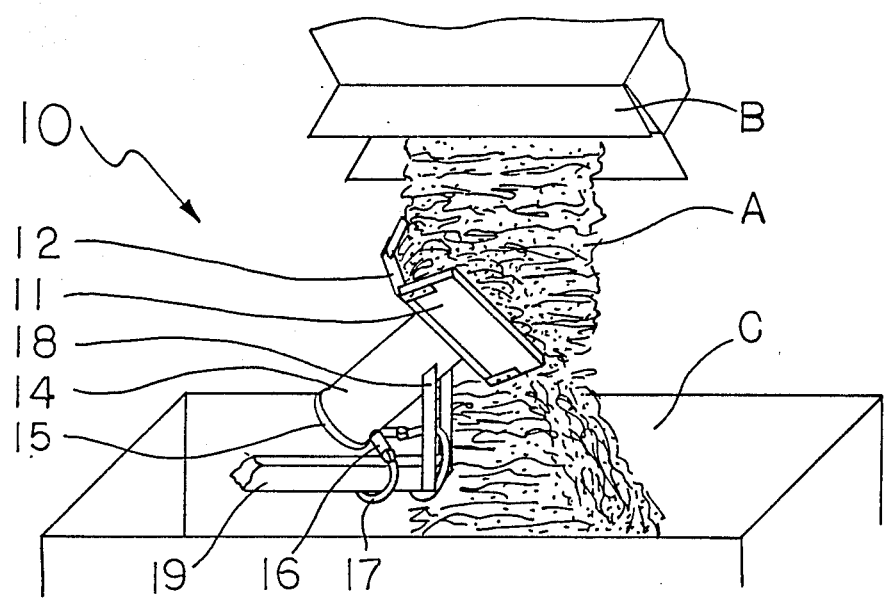
FIG. 2 is a perspective view showing the apparatus of the present invention in its measuring position during a manufacturing process.

It is an important aspect of the present invention that the design is such that the sampling position of the materials to be measured is a physical location where sampling integrity can be visually verified. In this respect, the mounting angle and sideboard geometry have been carefully selected to give the equivalent of an in-bin mounting, as in the prior art, in terms of density and void to solids ratio changes. As seen in FIG. 2, the apparatus is designed to be placed in a stream A of granular material from a discharge gate B as it falls into a weighing bin or the like C. In the manufacture of concrete, for example, the material in which moisture is to be measured may be sand or other aggregate materials to be used in the concrete. The discharge gate B may be associated with a weighing bin C in which an amount of sand is to be weighed prior to mixing the concrete batch. As can be seen the apparatus 10 of the present invention may be placed in the flowing stream A of material such that moisture measurement of the material is carried out as an inline process during manufacture.

The material A builds up on the sensing surface until the volume defined by the sensing surface 12 and sideboards 11 is full. It can be seen that the sensing surface 12 is disposed at an angle within the stream, and the sideboard geometry is such that the trough will continue to stay full while the material A is continuously moved through the measurement path by the momentum thereof from the force of gravity as it falls into bin C. The mounting bracket 18 is secured to housing 14 such that the sensing surface 12 is disposed at an angle of 30 to 55 degrees from vertical, as shown by the angle 0, with the optimum mounting angle being about 40 degrees. With such a mounting angle it has been found that the measuring volume stays constant while the material is continuously sampled wherein material A flows therethrough. In this manner, the moisture content of the entire amount or batch of material may be accurately determined as the sampling and measurement is carried out thereon. In concrete manufacture the discharge of the material from a discharge gate A into bin C may be as much as one thousand pounds of material per second, and the continuously sampled material may be measured at a suitable sampling interval as set by the measuring circuit to yield a more accurate moisture determination. For example, the moisture content of a ten cubic yard batch of sand or the like may be accurately determined by making about one hundred measurements thereof as it flows into the weigh hopper at such a discharge rate. The measurement sampling rate will, of course, have to be adjusted for different discharge rates.

Figure 3:
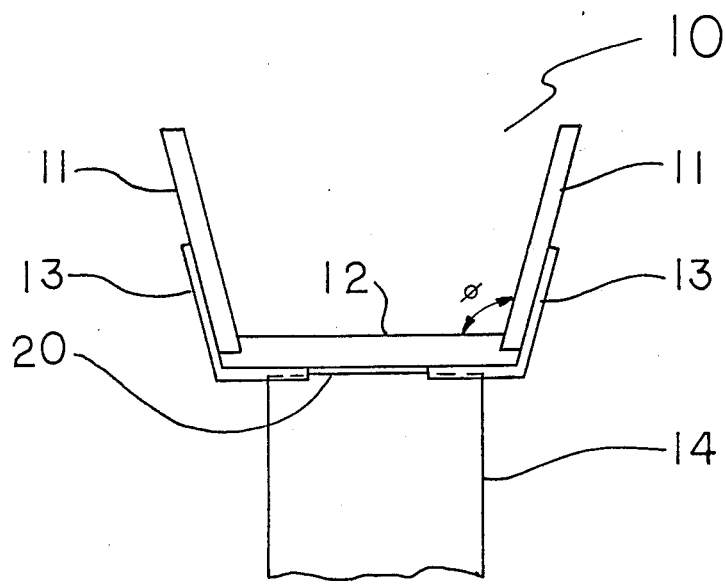
FIG. 3 is a front view of the apparatus showing the sideboard geometry thereof.

The more particular construction of the apparatus, as well as the sideboard geometry may be seen with reference to FIG. 3 wherein the measuring volume of the apparatus 10 is defined by sideboards 11 and measuring surface 12 secured by brackets 13. It can be seen that the sideboards are disposed at an angle of about 130 degrees relative to the measuring surface 12 as shown by the angle 0, to thereby define a measuring volume. The measuring volume may be 256 cubic inches, for example, wherein the measuring volume is about 4 by 8 by 8 inches and remains constant throughout sampling of the material. It is also seen that the angular position of the sideboards 11 help define the constant volume which is infinite as the material flows therethrough, and also reduces voids to solids variations by forcing the material falling thereon into the center of the trough. As mentioned hereinbefore, the sideboards 11 and measuring surface 12 are constructed of an ultra high molecular weight polyethylene wherein the sideboards may have the thickness of ½ inch, in the measuring surface 12 may have a thickness of ¾ inch. The housing 14, in which the electronic circuitry associated with the present invention is disposed, is sealed to the measuring surface 12 at the bottom side thereof by means of a neoprene or rubber gasket 20 which prevents any moisture from entering the housing 14. It is to be understood that the particular construction described is not intended to limit the present invention, and the dimensions and construction may be varied in accordance with the general teachings herein.

Figure 4:
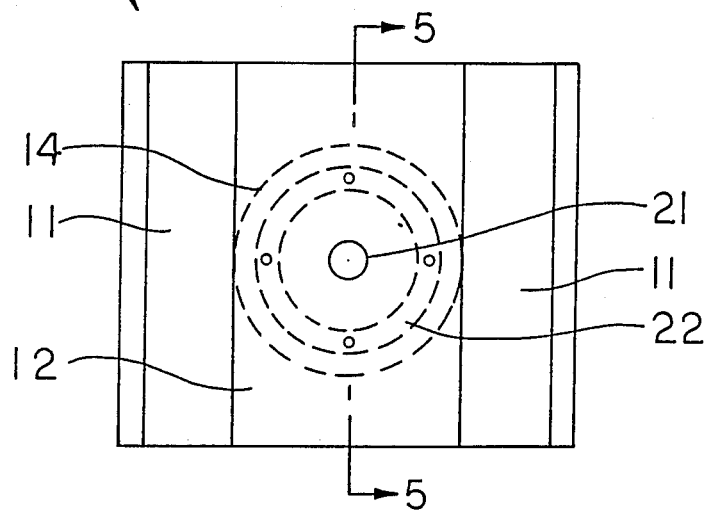
FIG. 4 is a top plan view of the apparatus showing the electrode arrangement of the sensing device.

Turning now to FIG. 4, the electrode configuration of the moisture measuring apparatus 10 is shown. The apparatus 10 utilizes a fringe electrode capacitance type gauge which is particularly suitable for mounting in he open space beneath a discharge gate as discussed in relation to FIG. 2. The measuring surface 12 disposed between sideboards 11 houses a center electrode 21 which is disposed flush with the upper surface of measuring surface 12. An outer ring electrode 22 is disposed around center electrode 21 forming the condenser plates of the capacitance gauge.

In accordance with the present invention, measurements depend upon the dielectric properties of the material passing over the measuring surface 12 and electrode configuration 21 and 22, wherein the power absorption by the material passing through the measuring system is a function of the moisture content of that material. In this manner, an accurate determination of the moisture content in the material may be obtained for a plurality of samples as the material continuously falls over the measuring surface 12.

Figure 5:
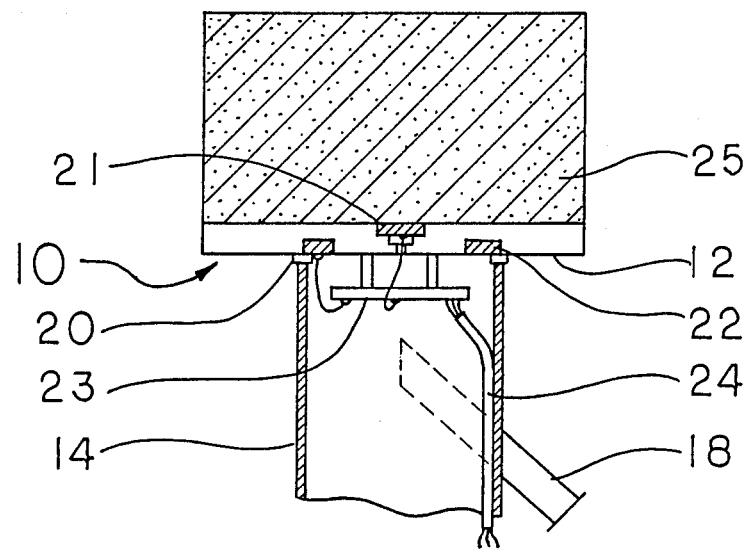
FIG. 5 is a cross-sectional view of the apparatus of the present invention taken along the line 5-5 of FIG. 4.

As seen in FIG. 5, the center electrode 21 is disposed flush with the upper surface of measuring surface 12 such that it is in contact with the material 25 to be measured. The outer ring electrode 22 is disposed in the lower surface of measuring surface 12, and surrounds the center electrode 21 thereby forming the capacitance gauge. The dielectric constant of the measuring surface 12 must be known in order to calibrate the gauge for an accurate determination of the moisture in material 25. The electrodes are conductively connected to a circuit board 23 forming the measuring circuitry of the present invention and disposed within housing 14 which acts as a shielding to the circuitry. The electronic circuitry of circuit board 23 is electrically connected to an outside display or other circuitry by means of cable 24 and input/output jacks 16 as shown in FIG. 1.

Referring now to FIG. 6, a circuit incorporated in the moisture measurement apparatus of this invention is shown in block diagram for general understanding of its function. The electrode configuration of the apparatus comprising center electrode 21 and outer ring electrode 22 is disposed adjacent a volume of material 25 in which moisture is to be measured. The outer ring electrode 22 is coupled to common ground and center electrode 21 is coupled to a bridge circuit 102 wherein the potential appearing across the electrode configuration may be measured. A conventional crystal oscillator 100, such as a Pierce oscillator, generates a frequency output which is delivered to a high frequency amplifier 101 and subsequently to bridge circuit 102. The bridge circuit 102 forms the capacitance impedance circuit including the capacitance electrode arrangement which will measure very minute capacitance variations. The capacitance variations to be measured by the measuring circuit of the present invention can be as little as four picofarads (PF), and thus the frequency generated by the oscillator 100 and introduced into the material must be very high in order to detect such capacitance variations. In the preferred embodiment, the Pierce oscillator 100 may generate a frequency of 3 to 6 megahertz (MHz) in which the amplitude of the oscillations is kept constant by means of peak regulator 103. The output of the bridge circuit is a DC voltage which is a function of the dielectric properties measured at the electrode configuration, and is amplified by amplifier 104. The amplified DC voltage is then fed to isolation circuitry to thereby isolate the measurement signal from earth ground. It is noted that the measurement signal cannot be referenced to earth ground, as an earth ground connection will upset the bridge balance in the measuring gauge. The isolation circuitry comprises a voltage-to-frequency convertor 105 which changes the DC voltage to a series of pulses proportional thereto which is then optically coupled to frequency-to-voltage conversion circuitry 106 wherein the frequency signal proportional to the output of the bridge circuitry is converted back into a DC voltage which has thereby been referenced to earth ground in order to be compatible with external circuitry such as power supplies or computer systems. The measurement signal is, thus, isolated from earth ground via this isolation circuit to avoid bridge imbalance as mentioned. This DC voltage is then amplified at amplifier 107 and output to a suitable display 108 where it may be scaled to read out percent moisture of the measured material by either dry or wet weight.

The particular measuring circuitry will be more fully described with reference to FIG. 7, wherein a measuring circuit which can be utilized with the present invention is shown schematically. To facilitate clarity, the circuit is divided into FIGS. 7a and 7b, wherein the lines at the right hand edge of FIG. 7a are continued with corresponding lines at the left hand edge of FIG. 7b. As noted hereinbefore, circuitry to be described is preferably mounted on a circuit board 23 within housing 14 as seen in FIG. 5, but may located at an external position and electrically coupled to the measuring apparatus. To facilitate an understanding thereof, the circuit of FIG. 7 will be described with reference of the functional units or blocks as shown in FIG. 6 and denoted by dashed lines.

Figure 7A:
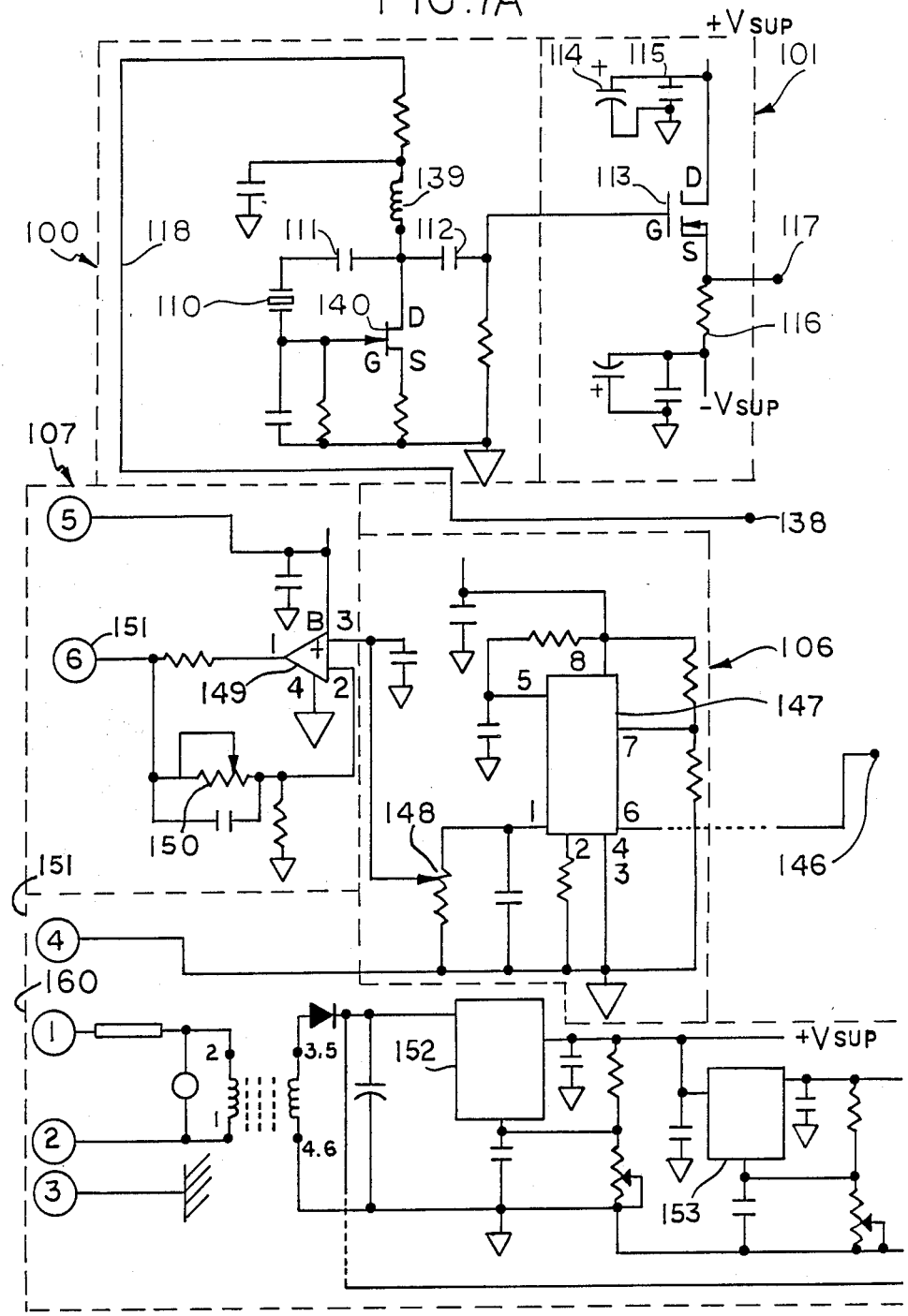

In FIG. 7a, the oscillator circuitry 100 comprises a generally known Pierce oscillator which utilizes a crystal 110 as a parallel resonant feedback circuit. The crystal 110 is connected to the gate of a junction MOSFET 140 with feedback through capacitor 111 in a known manner. The Pierce oscillator 100 output is connected to the gate of a power FET via series connected capacitor 112. The power FET 113 forms the basis of the high frequency amplifier section 101 in the measuring circuit. The drain of the FET 113 is connected to a voltage source and common ground via noise bypass circuitry. The noise bypass circuitry comprises parallel connected capacitors 114 and 115, which are utilized to extend the high frequency to the power supply input in a known manner. The capacitor 114 may be a tantalum-oxide capacitor and have a value of 1-2 micro-farads to inhibit high frequency noise at the polarizing point of the power supply input. The capacitor 115 may be a monoblock or similar capacitor having a value of 0.1 microfarads. This capacitor is utilized to absorb any leakage current from capacitor 114 in the noise bypass circuit. The power FET 113 is connected in somewhat of a source-follower configuration, wherein the source is connected to the negative voltage supply via load resistor 116, and a noise bypass circuit is also utilized as described above. The amplified high frequency oscillating signal generated by oscillator 100 is output from the high frequency amplifier 101 at terminal 117. It is noted that the return path 118 in the oscillator circuit 100 will act to maintain the amplitude of the oscillations constant as will be further described hereafter.

Referring now to FIG. 7b, the output of high frequency amplifier 101 at terminal 117 is connected via capacitor 119 to the bridge circuit 102 and referenced to ground via resistor 120. The output of the oscillator circuit is thereby coupled to a half-wave rectifier 121 and the positive voltage supplied to the material to be measured. The AC signal is also coupled via line 122 to the peak regulating circuit 103. As can be seen in FIG. 7b, the outer ring electrode 21 is connected to common ground and isolated from earth ground, and the center electrode 20 is coupled into the bridge circuit 102 at terminal 123. The voltage obtained from the measuring electrodes is referenced to ground and is coupled to terminal 124 via resistor 125. The measurement of the moisture content in material occurs as follows: First let us assume that there is no material in the measuring apparatus such that the free air capacity is measured. The free air capacity is about 4 picofarads so that a voltage of about 7 to 8 volts will be generated and applied to terminal 124. The AC signal supplied by the oscillator circuit 100 is also supplied to half-wave rectifier 126 via line 122. A negative voltage is generated by a very stable capacitor 127 and load resistor 128. The capacitor 127 may have a value of 4 picofarads such that the negative voltage generated will be a voltage of $-7$ to $-8$ volts which is also coupled to terminal 124. Thus, when no material is present, the voltage at terminal 24 will be zero. When a material is introduced to the measuring capacitor, the voltage produced will be increasingly positive with the amount of moisture present in the material, and the voltage at terminal 24 will go positive corresponding thereto. The DC voltage generated at terminal 124 is thus, moisture dependent. This voltage is applied to the non-inverting input of operational amplifier 104 and compared with a negative reference voltage generated at capacitor 127. Normally, the inverting input of operational amplifier 104 is utilized as the summing node, but here a high impedance input is necessary so the non-inverting input was used. For this reason, the resistors 125 and 128 must be matched for proper measurement. The capacitor 129 is coupled to a supply voltage and generates a reference voltage which can be adjusted by means of potentiometer 130 acting as a zero adjustment. The reference voltage is coupled to the inverting input of operational amplifier 104 via resistor 131. The operational amplifier 104 may be of the type LF 412.

In order to obtain accurate measurements of the small changes in capacitance due to moisture content of the material, the amplitude of the frequency signal generated in oscillator circuit 100 should be kept constant. A signal is obtained at terminal 132 which is a crude sine wave and must be maintained. This signal is coupled to a half-wave rectifier 133 as part of the peak regulating circuit 103. The rectified signal is then coupled to the inverting input of operational amplifier 134 via resistor 135. A reference voltage is supplied to the peak regulating circuit 103 by means of capacitor 136 by diode 133. The amplifier 134 acts to compare the amplitude of the oscillation signal obtained via rectifier 133 and capacitor 136 to a precision voltage source coupled to potentiometer 137, and connected to the non-inverting input of amplifier 134. The output of the amplifier 134 is controlled in this manner and is fed via terminal 138 to an RF choke 139 in oscillator circuit 100. The output of RF choke 139 is coupled to the drain of the junction MOSFET 140. The reference voltage from the peak regulator circuit 103 derived in this manner acts to feed the oscillator the necessary drive voltage to keep the oscillation amplitude equal to this reference voltage.

The reference voltage may be adjusted by means of potentiometer 137 acting as a peak to peak adjustment wherein a 20 volt peak to peak oscillation amplitude, for example, may be obtained and held constant.

Returning to the measurement signal generated in the bridge circuit 102 and amplified by amplifier 104, it is necessary to isolate this measurement signal from earth ground to avoid bridge imbalance in the circuit. Due to the placement of the measuring apparatus in a falling stream of granular material, a portion of the wet material is caused to fall on the housing 14 containing the electronic circuitry. The measurement signal may be disturbed by the presence of moisture on the housing, thus necessitating isolating the measurement signal from earth ground. The output from amplifier 104 is coupled to a voltage-to-frequency converter 105 via resistors 141 and 142. The voltage-to-frequency converter 105 comprises an integrated circuit 143 of the type LM 331. The amplified output voltage of bridge circuit 102 is coupled to pin 7 of the IC 143 which then acts as a voltage-to-frequency converter. The IC 143 will output a frequency at pin 3 proportional to the measurement voltage which is coupled to an LED 144. The LED 144 will produce a light pulse in accordance with the frequency signal obtained from voltage-to-frequency converter 143 and proportional to the moisture dependent voltage obtained at bridge circuit 102. This frequency signal will be optically coupled to a photocell 145, and is thereby converted back into a frequency signal in reference to earth ground. The light coupling device including LED 144 and photocell 145 may be of the type H11A1 and is utilized to achieve isolation of the measuring signal from earth ground.

The frequency signal is coupled to terminal 146 and is input to a frequency-to-voltage converter 106 as shown in FIG. 7a. The frequency-to-voltage converter 106 comprises an integrated circuit 137 of the type LM331 as in the voltage-to-frequency converter 105 as described hereinbefore. In this case, the circuit 147 is connected as a frequency-to-voltage converter to thereby transform the frequency signal obtained from circuit 105 via optical coupling to a voltage proportional to the moisture content measured at the electrodes of the apparatus. The output of the circuit 147 is coupled to potentiometer 148 wherein it is scaled and applied to the non-inverting input of operational amplifier 149. The output of amplifier 149 is applied to span potentiometer 150 which may be preset so the slope or sensitivity of the measuring circuit corresponds with a volume percentage of moisture in the measured material such as 4 volts per 10% moisture. A signal from potentiometer 150 is coupled to the inverting input of amplifier 149 and an output signal obtained at terminal 151 which may be coupled to an external display 108. By scaling the output in this manner, the calibration of the instrument will be simplified and will provide a sufficient starting point for such calibration.

As a matter of interest, calibration must be performed to correct for density changes in the capacitive moisture measurement of the present invention. The measuring method intrinsically measures volumetric moisture and not percent moisture by weight of the granular material, and could create density errors of 0.1 to 0.3 percent moisture by weight. Calibration is accomplished by referencing oven-dried samples and correlating with the measurement readings to set the zero reading in the instrument. The zero adjustment potentiometer is found in the bridge circuit at 130, and may be adjusted as necessary for offset control. During calibration, sand or other granular material with high and low moisture content is required for fine tuning of the output response in the measuring circuit.

Returning now to FIGS. 7a and 7b, a power supply for the circuit is shown by reference numeral 151. The power supply 151 provides bias and reference voltages to the measuring circuit and scales the moisture signal from the instrument to drive an external display. More specifically, the power supply 151 comprises an integrated circuit 152 of the type LM7815 positive which provides a positive supply voltage to the amplifiers and integrated circuits of the measuring circuit. Another integrated circuit 153 of the type LM317M reference provides a precision reference voltage supplied to critical parts of the system such as gain control or adjustment potentiometers. Similarly, an integrated circuit of the type LM7915 negative provides a negative supply voltage used in the operational amplifiers and other circuit components where noted.

Figure 8:
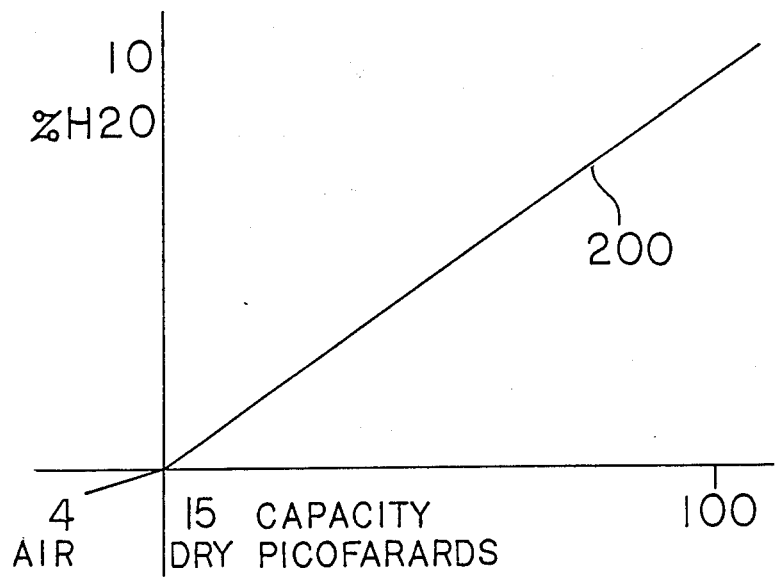
FIG. 8 is a graph showing the output of the measuring circuits described in relation to the present invention versus the amount of moisture measured in the granular material.

The measuring circuit as described above will provide a voltage which is proportional to the volumetric moisture measurement obtained at the electrode configuration of the measuring apparatus. As mentioned before, the instrument is calibrated such that an output voltage will be proportional to the particular percentage of moisture in the measured material. As can be seen with reference to FIG. 8, the capacitance variation versus the percentage of moisture is shown in the graph diagram. The curve 200 shown in the graph comprises a calibration curve associated with the particular granular material which is to be measured. Different granular materials will produce different calibration curves 200 and therefore, must be determined relative to the particular material. Once calibrated, the instrument will sample the granular material as it falls into and through the trough of the apparatus as previously described. In this manner, the output of the measuring circuit can be directly read as a percentage of moisture to thereby determine the moisture content of the entire batch of material. As can be seen from FIG. 8, the free air capacity of the gauge is about 4 picofarads, on dry sand about 15 picofarads, and on sand at 10% moisture, the capacity will be about 100 picofarads. It is, of course, recognized, that this curve is related to the measurement of moisture in the sand and other curves must be utilized with other aggregates or granular materials.

It can readily be seen that the present invention provides a very accurate and easily obtained moisture measurement of granular material in a very efficient manner. The present invention is especially advantageous as utilized in concrete products manufacturing, wherein the water content of a concrete mixture must be very accurately known in order to obtain the proper physical characteristics of the resulting concrete mixture. The present invention obtains these accurate results with an apparatus which may be placed in a position where sampling integrity may be visually verified. Additionally, the invention may be utilized as an in-line procedure which will not inhibit the normal manufacturing steps utilizing such granular materials.

It is to be understood that while the preferred embodiments of the present invention have been disclosed herein, it will be appreciated that modifications of these particular embodiments of the present invention may be resorted to without departing from the scope of the invention as found in the appended claims.

What is claimed is:

1. An apparatus for the measurement of the moisture content of a material comprising:
   a sensing surface having measuring means therein said measuring means comprising a first electrode means of electrically conductive material, a second electrode means of an electrically conductive material disclosed adjacent said first electrode means, wherein said first and second electrode means define a capacitive measuring means for determining the electrical properties of a material flowing over said surface;
   a pair of opposed sides extending from said sensing surface defining a space in which a substantially constant volume of said material will flow at a substantially constant density;
   said sensing surface being disposed in the path of said flowing material, such that the material will fall into and fill said space to continuously sample said volume of material as said material flows over said surface; and
   circuit means coupled with said measuring means for producing a signal corresponding to the moisture content of said continuously sampled volume of material.

2. An apparatus according to claim 1, wherein said sensing surface comprises a material which acts as an electrical insulator and which has a low and predictable dielectric constant.

3. An apparatus as in claim 1, wherein said sensing surface comprises a material which is abrasion resistant and has a low co-efficient of friction to said material flowing thereover.

4. An apparatus according to claim 1, wherein, said sensing surface comprises a material which has low water absorption so as not to effect the moisture measurement of said material.

5. An apparatus as in claim 1, wherein said sensing surface comprises an ultra-high molecular weight polyethelyne material having sufficient strength to support said volume of said material.

6. An apparatus according to claim 1, wherein said first and second electrodes are arranged in a fringe electrode capacitance type geometry wherein said first electrode comprises a generally planar body being disposed flush with said sensing surface, and said second electrode is a ring electrode having a planar configuration and being disposed such that it surrounds said first electrode and defines said capacitance cell.

7. An apparatus according to claim 1, wherein said sensing surface is disposed at an acute angle within said path of flowing material, and said material is continuously sampled.

8. An apparatus according to claim 1, wherein said material is made to fall into said space defined by said sensing surface and pair of opposed sides, such that said material will build up on said surface until said space is filled and a said volume of material will flow over said sensing surface within said space by the force of gravity.

9. An apparatus according to claim 1, wherein said pair of opposed sides extend at an angle of about 130 degrees relative to said sensing surface, to define said volume of said material and reduce voids to solids variations.

10. An apparatus according to claim 1, wherein said sensing surface is disposed at an angle from 30 to 55 degrees relative to vertical, thereby enabling sampling of said constant volume of said material flowing thereover by the force of gravity.

11. An apparatus according to claim 1, wherein said circuit means comprises an oscillator forming a tuned circuit in conjuction with said measuring means, whereby said circuit means generates a DC voltage which is proportional to the moisture content of said material located in said volume.

12. An apparatus according to claim 11 further comprising
   isolation circuit means for isolating said DC voltage proportional to said moisture content of the material from earth ground.

13. An apparatus according to claim 12, wherein said isolation circuit means comprising a voltage-to-frequency converter for producing a frequency signal proportional to the measure DC voltage;
   means for optically coupling said frequency signal to a frequency-to-voltage converter for producing an output DC voltage proportional to the moisture content of the measured material from said isolated DC voltage.

14. Apparatus according to claim 1, wherein said apparatus is positioned in the main stream of said material such that the measurement of the moisture content of a material carried out as an in-line step in a manufacturing process.

15. An apparatus according to claim 1, wherein a plurality of measurements are obtained from a plurality of samples of the material as it flows over said sensing surface to thereby obtain an accurate measurement of an entire batch of said material.

16. An apparatus according to claim 1, wherein said material to be measured is a granular material used in making concrete.

17. A method of measuring the moisture content of a material comprising the steps of:
   positioning a sensing surface having a measuring means in the path of a flowing material such that said material flows onto and over said sensing surface;
   said measuring means defining a measuring space comprising a first electrode means of electrically conductive material and a second electrode mean of an electrically conductive material disposed adjacent said first electrode means, wherein said first and second electrode means define a capacitive measuring means;
   continuously sampling a constant volume of said flowing material with said measuring means;
   measuring the moisture content of said constant volume of material by supplying high-frequency current to the material in said volume and deriving a voltage proportional to the moisture content thereof.

18. A method according to claim 17, wherein said space accommodates said constant volume of material, and is positioned in a falling main stream of said material such that said material continuously falls into and through said space.

19. A method according to claim 17, wherein said measuring means is positioned so that said sampling may be visually observed, and thereby sample integrity verified.

20. A method according to claim 17, wherein said sensing surface is positioned at an acute angle to said flowing material such that said material will build up on said surface until said space is filled and a said volume of material will flow over said sensing surface by the force of gravity.

21. A method according to claim 17, wherein
said measuring step further comprises isolating said voltage proportional to the moisture content from earth ground.

22. A method according to claim 17, further comprising
making a plurality of measurements of the moisture content in the material to thereby accurately determine the total moisture content in a batch of said material.

23. A method according to claim 17, wherein
said material is a granular material utilized in the manufacture of concrete, and said measuring of the moisture content thereof is carried out as an in-line step in the manufacturing process.

* * * * *